United States Patent
Ikuma et al.

(10) Patent No.: US 9,918,614 B2
(45) Date of Patent: Mar. 20, 2018

(54) ENDOSCOPE SYSTEM WITH ANGLE-OF-VIEW DISPLAY INFORMATION OVERLAPPED ON THREE-DIMENSIONAL IMAGE INFORMATION

(71) Applicant: OLYMPUS CORPORATION, Tokyo (JP)

(72) Inventors: Soichi Ikuma, Akishima (JP); Tatsuro Yamamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/244,270

(22) Filed: Aug. 23, 2016

(65) Prior Publication Data
US 2016/0353968 A1 Dec. 8, 2016

Related U.S. Application Data

(63) Continuation of application No. PCT/JP2015/062830, filed on Apr. 28, 2015.

(30) Foreign Application Priority Data

Jun. 10, 2014 (JP) ................................ 2014-119754

(51) Int. Cl.
*A61B 1/04* (2006.01)
*A61B 1/00* (2006.01)
(Continued)

(52) U.S. Cl.
CPC .............. *A61B 1/0005* (2013.01); *A61B 1/00* (2013.01); *A61B 1/00009* (2013.01); *A61B 1/04* (2013.01);
(Continued)

(58) Field of Classification Search
CPC ..... A61B 1/0005; A61B 1/00; A61B 1/00009; A61B 1/04; A61B 5/06; A61B 5/7425; A61B 5/743; G02B 23/24
See application file for complete search history.

(56) References Cited

U.S. PATENT DOCUMENTS

| | | | | | |
|---|---|---|---|---|---|
| 4,712,133 | A | * | 12/1987 | Kikuchi | ............... H04N 1/2112 348/211.99 |
| 2004/0210105 | A1 | * | 10/2004 | Hale | .................. A61B 1/00183 600/101 |

(Continued)

FOREIGN PATENT DOCUMENTS

| EP | 2 554 103 A1 | 2/2013 |
|---|---|---|
| EP | 2 823 784 A1 | 1/2015 |

(Continued)

OTHER PUBLICATIONS

International Search Report dated Aug. 11, 2015 issued in corresponding International Patent Application No. PCT/JP2015/062830.

(Continued)

*Primary Examiner* — John P Leubecker
(74) *Attorney, Agent, or Firm* — Scully, Scott, Murphy & Presser, P.C.

(57) ABSTRACT

An endoscope system includes a portion configured to acquire a position of an objective optical system provided in an insertion portion of an endoscope; a portion configured to position the position of the objective optical system on three-dimensional image information about a subject; a portion configured to generate angle-of-view display information related to a picked-up image picked up by an image pickup system including the objective optical system; an instruction portion configured to output an instruction signal; and an image processing portion configured to create an overlapped image obtained by overlapping the angle-of-view display information at a position on the three-dimen- (Continued)

sional image information corresponding to the position of the objective optical system at a time point of inputting the instruction signal.

9 Claims, 10 Drawing Sheets

(51) Int. Cl.
   *G02B 23/24* (2006.01)
   *A61B 5/06* (2006.01)
   *A61B 5/00* (2006.01)

(52) U.S. Cl.
   CPC ............... *A61B 5/06* (2013.01); *G02B 23/24* (2013.01); *A61B 5/743* (2013.01)

(56) References Cited

U.S. PATENT DOCUMENTS

| | | | | |
|---|---|---|---|---|
| 2006/0126920 | A1* | 6/2006 | Rust | G06T 19/00 382/154 |
| 2006/0189842 | A1* | 8/2006 | Hoeg | A61B 1/0005 600/118 |
| 2006/0281971 | A1* | 12/2006 | Sauer | A61B 34/20 600/109 |
| 2008/0287790 | A1* | 11/2008 | Li | A61B 5/062 600/437 |
| 2012/0155731 | A1* | 6/2012 | Weersink | A61N 5/103 382/131 |
| 2013/0023730 | A1 | 1/2013 | Kitamura et al. | |
| 2013/0250081 | A1* | 9/2013 | Pandey | H04N 7/18 348/77 |
| 2013/0257865 | A1* | 10/2013 | Kobayashi | A61B 6/466 345/419 |
| 2014/0088357 | A1* | 3/2014 | Ikuma | A61B 1/00009 600/109 |
| 2014/0282008 | A1* | 9/2014 | Verard | G03H 1/00 715/728 |
| 2015/0051617 | A1 | 2/2015 | Takemura et al. | |
| 2015/0057498 | A1* | 2/2015 | Akimoto | A61B 1/00009 600/103 |
| 2015/0223670 | A1* | 8/2015 | Fujita | A61B 1/00036 600/109 |
| 2016/0073927 | A1* | 3/2016 | Akimoto | A61B 1/00009 600/109 |
| 2016/0199148 | A1* | 7/2016 | Maracaja-Neto | A61B 1/00147 600/424 |
| 2017/0014017 | A1* | 1/2017 | Obara | A61B 1/00009 |

FOREIGN PATENT DOCUMENTS

| | | | |
|---|---|---|---|
| EP | 3 040 015 | A1 | 7/2016 |
| JP | 2003-225195 | A | 8/2003 |
| JP | 2005-312770 | A | 11/2005 |
| JP | 2009-279251 | A | 12/2009 |
| JP | 2011-212244 | A | 10/2011 |
| JP | 2012-110549 | A | 6/2012 |
| JP | 2013-027697 | A | 2/2013 |
| JP | 2013-085593 | A | 5/2013 |
| JP | 2013-202313 | A | 10/2013 |
| WO | 2011/122032 | A1 | 10/2011 |
| WO | 2012/176854 | A1 | 12/2012 |
| WO | 2013/145730 | A1 | 10/2013 |
| WO | WO 2014065336 | A1 * | 5/2014 ......... A61B 1/00036 |
| WO | 2015/029970 | A1 | 3/2015 |
| WO | 2015/049962 | A1 | 4/2015 |

OTHER PUBLICATIONS

Extended Supplementary European Search Report dated Aug. 10, 2017 in European Patent Application No. 15 80 6951.8.

* cited by examiner

ENDOSCOPE SYSTEM WITH ANGLE-OF-VIEW DISPLAY INFORMATION OVERLAPPED ON THREE-DIMENSIONAL IMAGE INFORMATION

CROSS REFERENCE TO RELATED APPLICATION

This application is a continuation application of PCT/JP2015/062830 filed on Apr. 28, 2015 and claims benefit of Japanese Application No. 2014-119754 filed in Japan on Jun. 10, 2014, the entire contents of which are incorporated herein by this reference.

BACKGROUND OF THE INVENTION

1. Field of the Invention

The present invention relates to an endoscope system capable of observing a luminal organ with reference to luminal organ image information in constructed three-dimensional image information, and a method for operating the endoscope system.

2. Description of the Related Art

An endoscope apparatus is widely used, for example, as a medical endoscope for performing observation of an organ in a body cavity or treatment using a treatment instrument when necessary. In the case of performing observation or treatment with such an endoscope apparatus, it is necessary to insert an insertion portion of the endoscope into a lumen and cause a distal end portion of the insertion portion to reach a destination such as a lesion quickly and accurately.

Therefore, in order to cause the insertion portion of the endoscope to reach a destination, a navigation technique has been conventionally proposed in which a navigation image is displayed as a guide.

For example, Japanese Patent Application Laid-Open Publication No. 2012-110549 describes a technique of identifying a correspondence relationship between visual point positions of a virtual endoscopic image and an actual endoscopic image, for example, based on a distance from an end point of an observation route, and simultaneously displaying the virtual endoscopic image and the actual endoscopic image by placing them side by side, overlapping them with each other so that their center positions are overlapped, or the like.

Further, Japanese Patent Application Laid-Open Publication No. 2011-212244 describes a technique of determining a visual point, central line-of-sight vector, and angle of view of a virtual endoscope based on a position, central line-of-sight vector, and angle of view of an endoscope, in consideration of a position of a structure of interest, and generating a virtual endoscopic image from a three-dimensional medical image.

In a conventional navigation system, it is possible to judge whether or not an endoscope distal end to be a visual point has been inserted to a desired position, and, at this time, it is also possible to judge not only a position of the visual point but also a line-of-sight direction from the visual point from a navigation image.

By the way, there are luminal organs having a plurality of branched lumens, such as a bronchus and a kidney.

For example, in a kidney, among those luminal organs, there may be a case where a stone occurs. Treatment for removing such a stone is performed with use of a treatment instrument or the like which projects from a distal end of an endoscope while an inside of a pelvis of the kidney and an inside of a kidney calyx are being observed with the endoscope.

SUMMARY OF THE INVENTION

An endoscope system according to a certain aspect of the present invention includes: an endoscope having an insertion portion to be inserted into a subject; an objective optical system provided in the insertion portion and configured to form an optical image of an inside of the subject; a position information acquiring portion configured to acquire position information about the objective optical system; a positioning portion configured to position the position information acquired by the position information acquiring portion relative to three-dimensional image information related to the subject; an angle-of-view display information generating portion configured to generate angle-of-view display information showing angle-of-view information about a picked-up image picked up by an image pickup system including the objective optical system; an instruction portion configured to be operable by a user and output an instruction signal giving an instruction to overlap the angle-of-view display information generated by the angle-of-view display information generating portion on the three-dimensional image information; and an image processing portion configured to create an overlapped image obtained by overlapping the angle-of-view display information at a position on the three-dimensional image information corresponding to the position information about the objective optical system acquired at a time point of inputting the instruction signal by the instruction portion.

A method for operating an endoscope system according to a certain aspect of the present invention is a method for operating an endoscope system including an endoscope, an objective optical system, a position information acquiring portion, a positioning portion, an angle-of-view display information generating portion, an instruction portion and an image processing portion, the method including the steps of: the objective optical system provided in an insertion portion of the endoscope forming an optical image of an inside of a subject; the position information acquiring portion acquiring position information about the objective optical system; the positioning portion positioning the position information acquired by the position information acquiring portion relative to three-dimensional image information related to the subject; the angle-of-view display information generating portion generating angle-of-view display information showing angle-of-view information about a picked-up image picked up by an image pickup system including the objective optical system; the instruction portion configured to be operable by a user outputting an instruction signal giving an instruction to overlap the angle-of-view display information generated by the angle-of-view display information generating portion on the three-dimensional image information; and the image processing portion creating an overlapped image obtained by overlapping the angle-of-view display information at a position on the three-dimensional image information corresponding to the position information about the objective optical system acquired at a time point of inputting the instruction signal by the instruction portion.

DETAILED DESCRIPTION OF THE PREFERRED EMBODIMENT(S)

Embodiments of the present invention will be described below with reference to drawings.

First Embodiment

Figure 1:
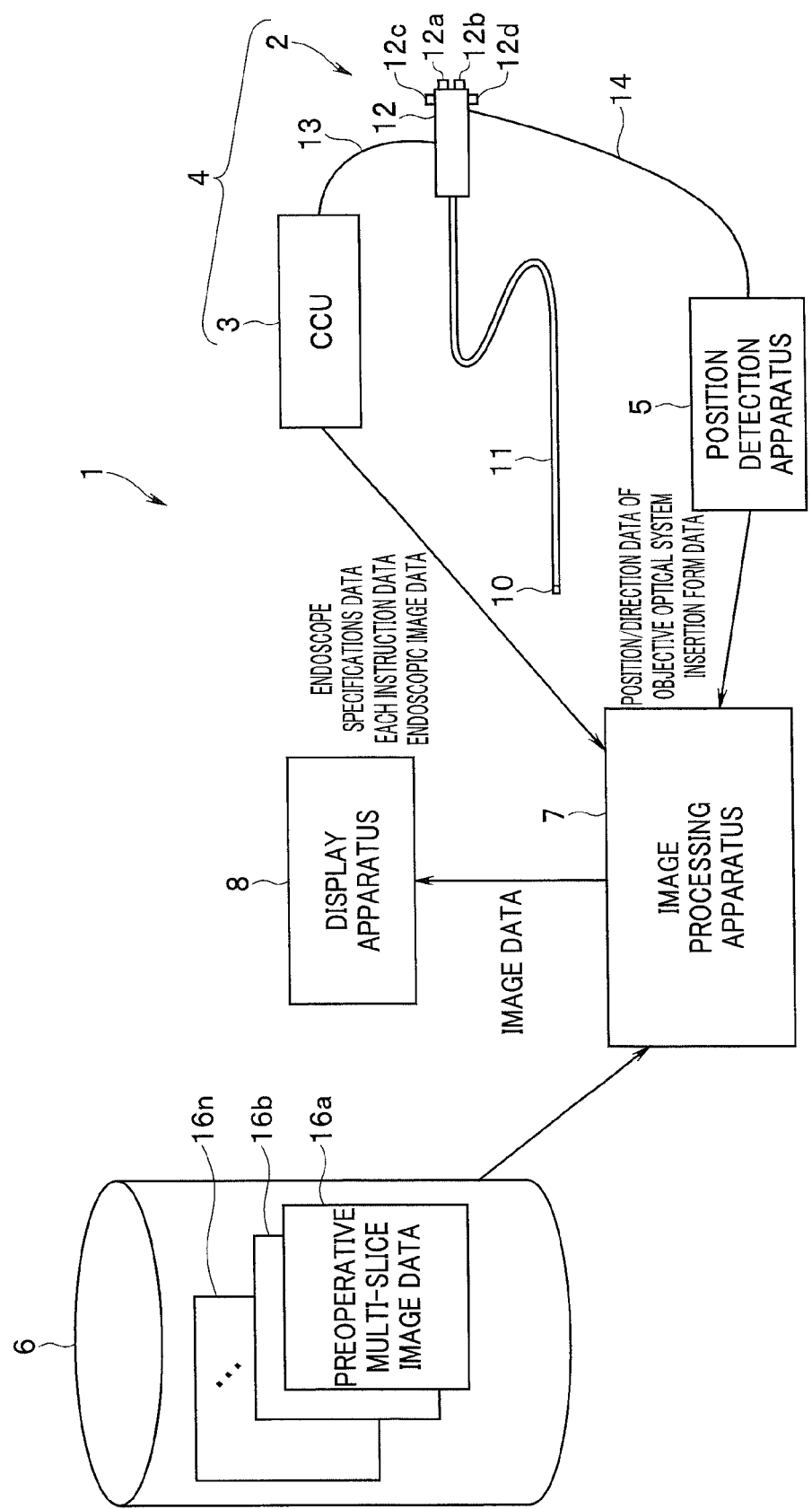
FIG. 1 is a diagram showing a configuration of an endoscope system in a first embodiment of the present invention.

FIGS. 1 to 11 show a first embodiment of the present invention, and FIG. 1 is a diagram showing a configuration of an endoscope system 1.

As shown in FIG. 1, the endoscope system 1 is provided with an endoscope apparatus 4 having an endoscope 2 and a camera control unit (CCU) 3, a position detection apparatus 5, a server 6, an image processing apparatus 7 and a display apparatus 8.

The endoscope 2 is provided with an elongated insertion portion 11 having flexibility of being inserted into a subject, an operation portion 12 connected to a proximal end portion of the insertion portion 11, and a cable 13 extended from a side surface of the operation portion 12.

The operation portion 12 is provided with a release button 12a which is an image pickup instruction portion configured to cause image pickup instruction data for acquiring a picked-up image to be recorded, to be generated (configured so that an image pickup instruction is inputted), an angle-of-view display button 12b configured to cause angle-of-view display instruction data for displaying an angle of view of an image of a subject being observed, to be generated (configured so that an angle-of-view display instruction is inputted), a freeze angle-of-view display button 12c which is an acquisition instruction portion configured to cause freeze angle-of-view display instruction data for displaying an angle of view at a time point of being operated, to be generated during a period of being enabled, to be generated (configured so that a freeze angle-of-view display instruction is inputted), and an accumulated angle-of-view display button 12d which is an accumulated display instruction portion configured to cause accumulated angle-of-view display instruction data for accumulating and displaying past angle-of-view display information to be generated (configured so that an accumulated angle-of-view display instruction is inputted). Here, the angle-of-view display button 12b is an overlapped image selection instruction portion configured so that a selection instruction for selecting on/off of overlapped image generation is inputted.

Note that each of the buttons 12a to 12d as described above are not limited to being provided on the operation portion 12 of the endoscope 2. For example, the buttons 12a to 12d may be provided as foot switches or may be provided as switches or the like in other configurations.

At a distal end portion of the insertion portion 11, an image pickup system 10 for picking up an image of an inside of a subject is provided. More specifically, the image pickup system 10 is provided with an objective optical system configured to form an optical image of the inside of the subject, and an image pickup device, such as a CCD, configured to perform photoelectrical conversion of the optical image formed by the objective optical system to generate an image pickup signal. The endoscope 2 is connected to the CCU 3 via the cable 13, and an image pickup signal of image pickup by the image pickup system 10 is transmitted to the CCU 3.

The CCU 3 performs predetermined image processing for the image pickup signal transmitted from the endoscope 2 to generate endoscopic image data. Further, the CCU 3 generates endoscope specifications data including angle-of-view information, based on a model number and the like of the connected endoscope 2 and an operation state of the endoscope apparatus 4. Here, for example, in a case where electronic zoom is performed by the image processing of the CCU 3, an angle-of-view range of an observed image changes. Further, in a case where the endoscope 2 is provided with a zoomable objective optical system also, the angle-of-view range changes. Therefore, as the angle-of-view information, real time data at time of transmission is used.

Further, from the distal end portion to proximal end portion of the insertion portion 11, a plurality of receiving coils not shown are provided at predetermined intervals. Each of the plurality of receiving coils outputs an electric signal according to a magnetic field generated by the position detection apparatus 5. The endoscope 2 is connected to the position detection apparatus 5 via a cable 14, and the respective electric signals outputted from the receiving coils are transmitted to the position detection apparatus 5.

The position detection apparatus 5 as a position information acquiring portion calculates and acquires position information (the position information includes each of pieces of information about a three-dimensional position of the objective optical system and an optical axis direction of the objective optical system) about a distal end of the insertion portion 11, more specifically, the objective optical system (which, otherwise, can be said to be a visual point) in the image pickup system 10, based on electric signals from receiving coils provided at the distal end portion of the insertion portion 11, among the plurality of receiving coils.

The acquisition of the position information by the position detection apparatus 5 is repeatedly performed, for example, at each predetermined time interval.

Then, the position detection apparatus 5 calculates and acquires insertion form data showing an insertion form of the insertion portion 11 based on the electric signals from the plurality of receiving coils described above. Note that, though bending form data is acquired with use of the receiving coils here, it is not limited to this, and the bending form data may be acquired with use of an FBG (fiber Bragg grating) sensor or the like.

The CCU 3, the position detection apparatus 5 and the server 6 described above are connected to the image processing apparatus 7. The server 6, among these, is connected to the image processing apparatus 7, for example, via a communication circuit such as a LAN inside a hospital.

The CCU 3 transmits the endoscopic image data, the endoscope specifications data, and the respective instruction data such as the image pickup instruction data, angle-of-view display instruction data, freeze angle-of-view display instruction data and accumulated angle-of-view display instruction data described above, to the image processing apparatus 7.

The position detection apparatus 5 transmits the position information (position and direction data) about the objective optical system and the insertion form data of the insertion portion 11 to the image processing apparatus 7.

On the other hand, the server 6 stores, for example, pieces of preoperative multi-slice image data 16a to 16n acquired in advance by CT, MRI, PET or the like before examination by the endoscope system 1 is performed. The server 6 transmits the pieces of preoperative multi-slice image data 16a to 16n to the image processing apparatus 7. Note that, though the image processing apparatus 7 reads the pieces of preoperative multi-slice image data 16a to 16n from the server 6 here, the pieces of preoperative multi-slice image data 16a to 16n may be, of course, read from a portable recording medium such as a CD-ROM in which the pieces of preoperative multi-slice image data 16a to 16n are caused to be recorded.

Based on each of the pieces of data acquired from the CCU 3, the position detection apparatus 5 and the server 6, the image processing apparatus 7 performs a process to be described later to create image data.

The image processing apparatus 7 is connected to the display apparatus 8, and the display apparatus 8 receives and displays the image data created by the image processing apparatus 7. The display apparatus 8 is a display portion configured to display an overlapped image created by the image processing apparatus 7 as described later.

Figure 2:
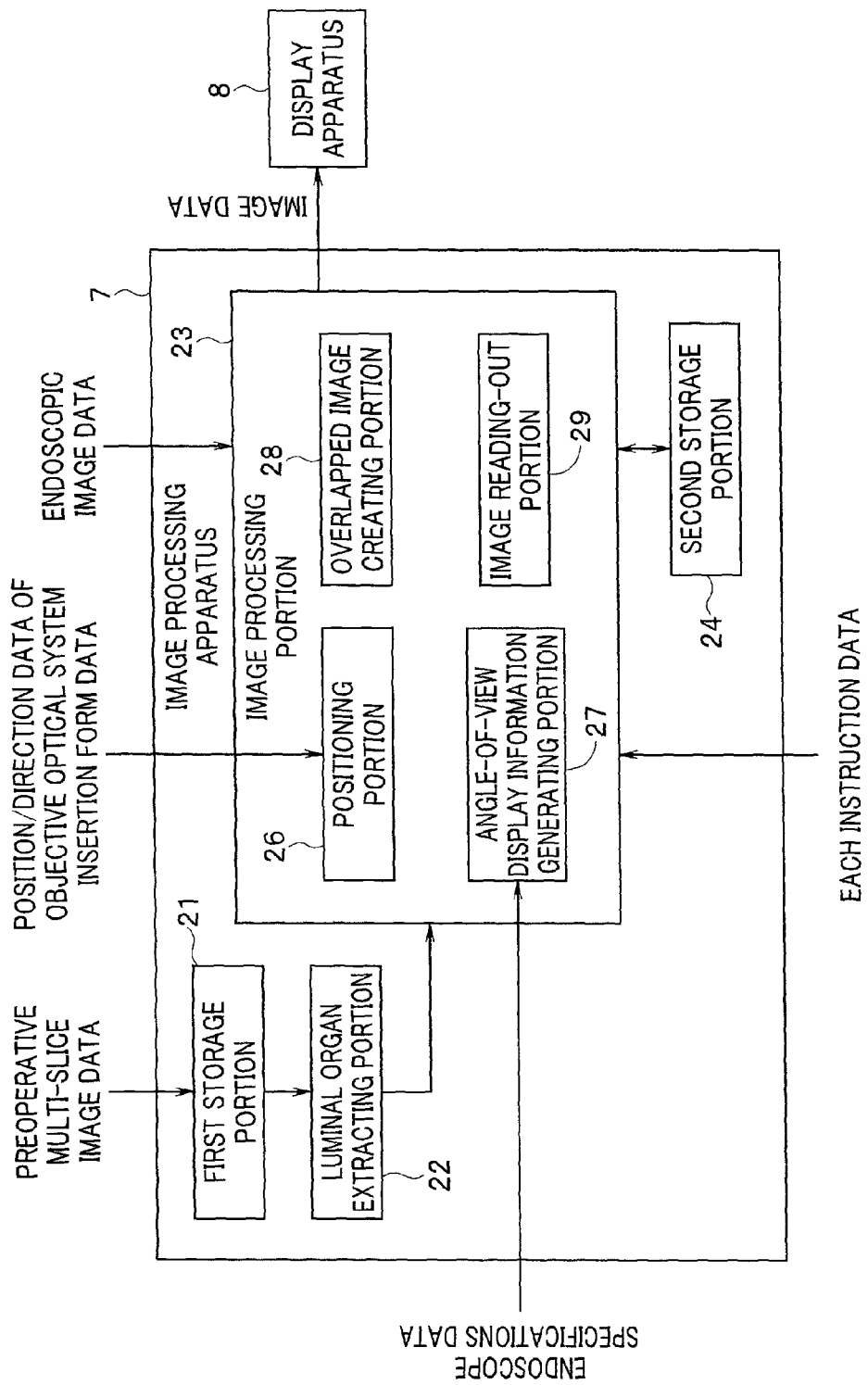
FIG. 2 is a block diagram showing a configuration of an image processing apparatus of the first embodiment.

Next, FIG. 2 is a block diagram showing a configuration of the image processing apparatus 7.

The image processing apparatus 7 is provided with a first storage portion 21, a luminal organ extracting portion 22, an image processing portion 23 and a second storage portion 24.

The first storage portion 21 stores the pieces of preoperative multi-slice image data 16a to 16n which are image information about a subject acquired in advance and which is for constructing three-dimensional image information.

The luminal organ extracting portion 22 reads out the image information stored in the first storage portion 21 to construct three-dimensional image information, and, moreover, extracts predetermined luminal organ image information present in the three-dimensional image information. Here, the extracted luminal organ image information is assumed to be image information showing a luminal structure of a kidney. At this time, the luminal organ extracting portion 22 extracts, for example, a predetermined luminal organ including a ureter 42, a pelvis of kidney 43, a major calyx 44, minor calyxes 45, renal papillae 46 (moreover, a urinary bladder and a urethra when necessary) as a luminal organ 41 (see FIG. 4).

The image processing portion 23 is provided with a positioning portion 26, an angle-of-view display information generating portion 27, an overlapped image creating portion 28 and an image reading-out portion 29.

The positioning portion 26 positions the position information (including the position information about the objective optical system) acquired by the position detection apparatus 5 relative to the predetermined luminal organ image information as the three-dimensional image information extracted by the luminal organ extracting portion 22. The positioning by the positioning portion 26 is performed, for example, by calculation of a conversion equation for conversion from actual space coordinates acquired by the position detection apparatus 5 to three-dimensional image coordinates in which the three-dimensional image information is constructed.

Note that a method for the positioning is not limited to the method using the conversion expression described above, and, for example, a positioning method based on detection of positions of characteristic points on a body surface of a patient and specification of the characteristic points on three-dimensional image data, as is disclosed in Japanese Patent Application Laid-Open Publication No. 2005-312770, or a positioning method by matching between an endoscopic image and a virtual endoscopic image as disclosed in Japanese Patent Application Laid-Open Publication No. 2009-279251 may be adopted.

The angle-of-view display information generating portion 27 generates angle-of-view display information showing angle-of-view information about a picked-up image picked up by the image pickup system 10 including the objective optical system, based on the angle-of-view information in the endoscope specifications data received from the CCU 3. More specifically, the angle-of-view display information generated by the angle-of-view display information generating portion 27 is such that includes boundary lines showing an angle-of-view range, which extend from one point as a starting point. As specific examples, a fan shape, a cone shape, a quadrangular pyramid shape and the like are given. Here, the fan shape is suitable to be overlapped, for example, on two-dimensional image information created from the three-dimensional image information; the cone shape is suitable to be overlapped on the three-dimensional image information; and the quadrangular pyramid shape is suitable to be overlapped on the three-dimensional image information in consideration of a shape of an image pickup surface of the image pickup device (commonly a quadrilateral).

The image processing portion 23 sets the starting point of the boundary lines in the angle-of-view display information to a position of the objective optical system shown by the position information positioned by the positioning portion 26.

The overlapped image creating portion 28 of the image processing portion 23 overlaps the angle-of-view display information generated by the angle-of-view display information generating portion 27 at the position shown by the position information positioned by the positioning portion 26 in the predetermined luminal organ image information to create an overlapped image.

Once turning on of overlapped image generation is selected by the angle-of-view display button 12b, the creation of the overlapped image by the overlapped image creating portion 28 is performed in response to acquisition of position information by the position detection apparatus 5 repeatedly performed at each predetermined time interval as described above until turning off of overlapped image generation is selected. At this time, the display apparatus 8 displays the overlapped image while the overlapped image generation is turned on by the selection instruction. Thereby, the angle-of-view display information is displayed in real time. Further, when turning off of overlapped image generation is selected by the angle-of-view display button 12b, the overlapped image creating portion 28, for example, does not generate the overlapped image (however, in a case of storing overlapped images in the second storage portion 24 and performing accumulated angle-of-view display described below, as described later, the overlapped image may be created irrespective of an operation state of the angle-of-view display button 12b).

In preparation for a case of the accumulated angle-of-view display button 12d being operated, the overlapped image creating portion 28 creates the overlapped image in response to acquisition of the position information by the position detection apparatus 5 repeatedly performed at each predetermined time interval.

On the other hand, when the freeze angle-of-view display button 12c is operated, the overlapped image creating portion 28 only has to create the overlapped image at a time point of the operation being performed.

Further, an overlapping process by the overlapped image creating portion 28 is performed in a case of overlapping the angle-of-view display information on the predetermined luminal organ image information as the three-dimensional image information extracted by the luminal organ extracting portion 22 and in a case of creating the predetermined luminal organ image information as two-dimensional image information from the predetermined luminal organ image information as the three-dimensional image information as a bird's-eye image or a cutout image and then overlapping the angle-of-view display information.

If a created overlapped image is a two-dimensional image, the two-dimensional overlapped image becomes image data to be outputted to the display apparatus 8. If the created overlapped image is three-dimensional image, the image processing portion 23 creates a two-dimensional overlapped image such as a bird's-eye image or a cutout image from the overlapped image and causes the two-dimensional overlapped image to be the image data to be outputted to the display apparatus 8.

The second storage portion 24 stores at least one of the created two-dimensional overlapped image, and the position information and the angle-of-view information (more specifically, the position information (position and direction data) about the objective optical system and the angle-of-view information about the picked-up image, which are data for creating a two-dimensional overlapped image based on the pieces of preoperative multi-slice image data 16a to 16n stored in the server 6).

Here, it is recommended that, for the purpose of making it easy to grasp later a position at which and a direction in which a record photograph to be put on a patient's chart is photographed, the second storage portion 24 performs the storage of at least one of the two-dimensional overlapped image, and the position information and the angle-of-view information in association with a picked-up image picked up by the image pickup system 10. It is recommended that, at this time, a timing of the associated storage being performed includes a timing of an image pickup instruction having been inputted from the release button 12a, which is the image pickup instruction portion.

The image reading-out portion 29 outputs the two-dimensional overlapped image read out from the second storage portion 24 or the two-dimensional overlapped image created based on the position information and angle-of-view information read out from the second storage portion 24 to the display apparatus 8 for display. Freeze angle-of-view display instruction data caused to be generated by the freeze angle-of-view display button 12c, which is the acquisition instruction portion described above, is an acquisition instruction for acquiring information from the second storage portion 24.

Therefore, in response to an acquisition instruction, the image reading-out portion 29 reads out a two-dimensional overlapped image at a time point of starting to input the acquisition instruction from the second storage portion 24.

Otherwise, in response to an acquisition instruction, the image reading-out portion 29 reads out position information and angle-of-view information at a time point of starting to input the acquisition instruction from the second storage portion 24 and causes the image processing portion 23 to create a two-dimensional overlapped image based on the read-out position information and angle-of-view information.

Then, the image reading-out portion 29 continues to output the two-dimensional overlapped image for display while the acquisition instruction is effective. Thereby, during a period during which the acquisition instruction is effective, an angle of view at a time point of the freeze angle-of-view display button 12c being operated continues to be displayed.

Figure 3:
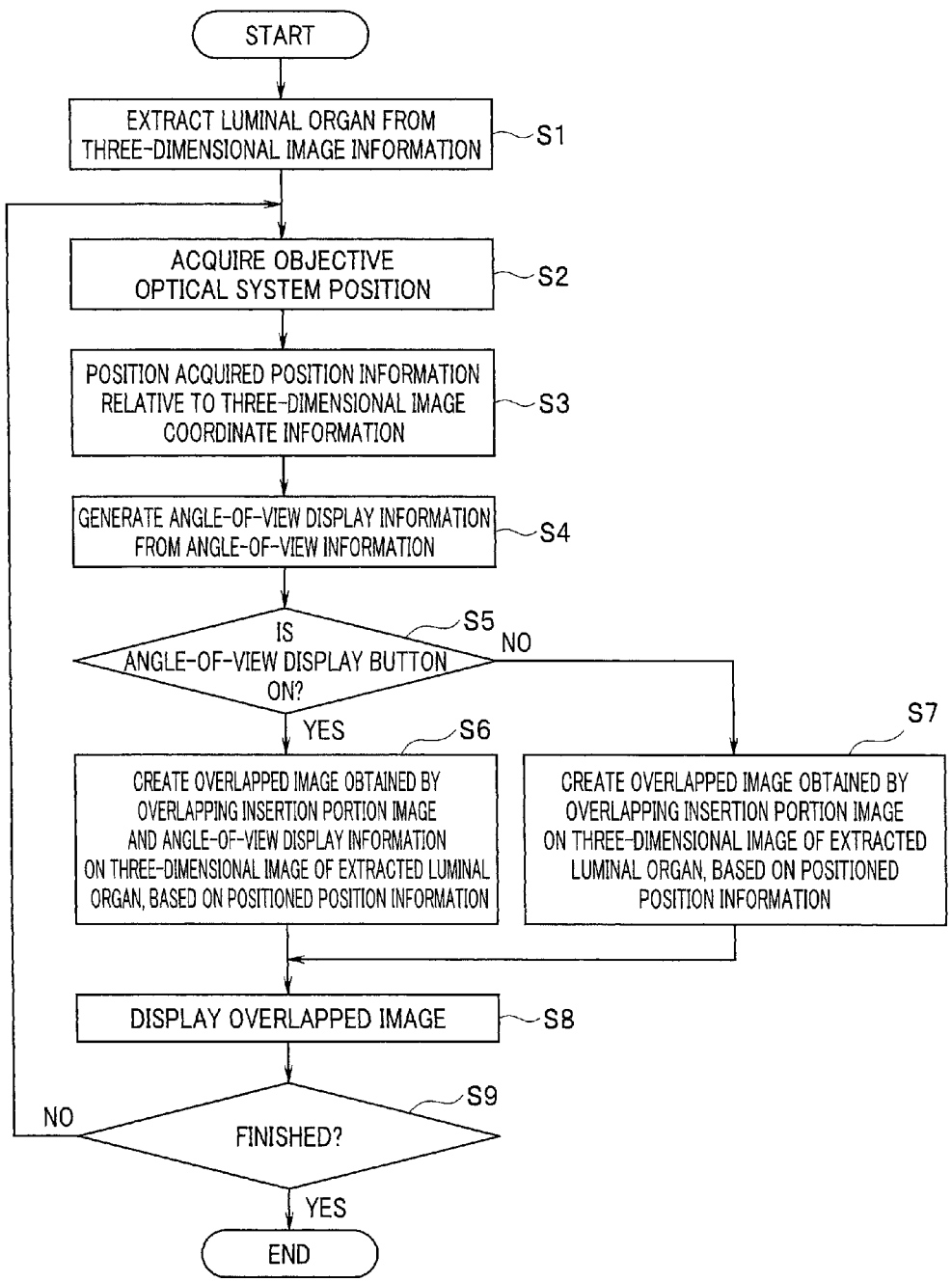
FIG. 3 is a flowchart showing operation of the endoscope system in the first embodiment.
Figure 4:
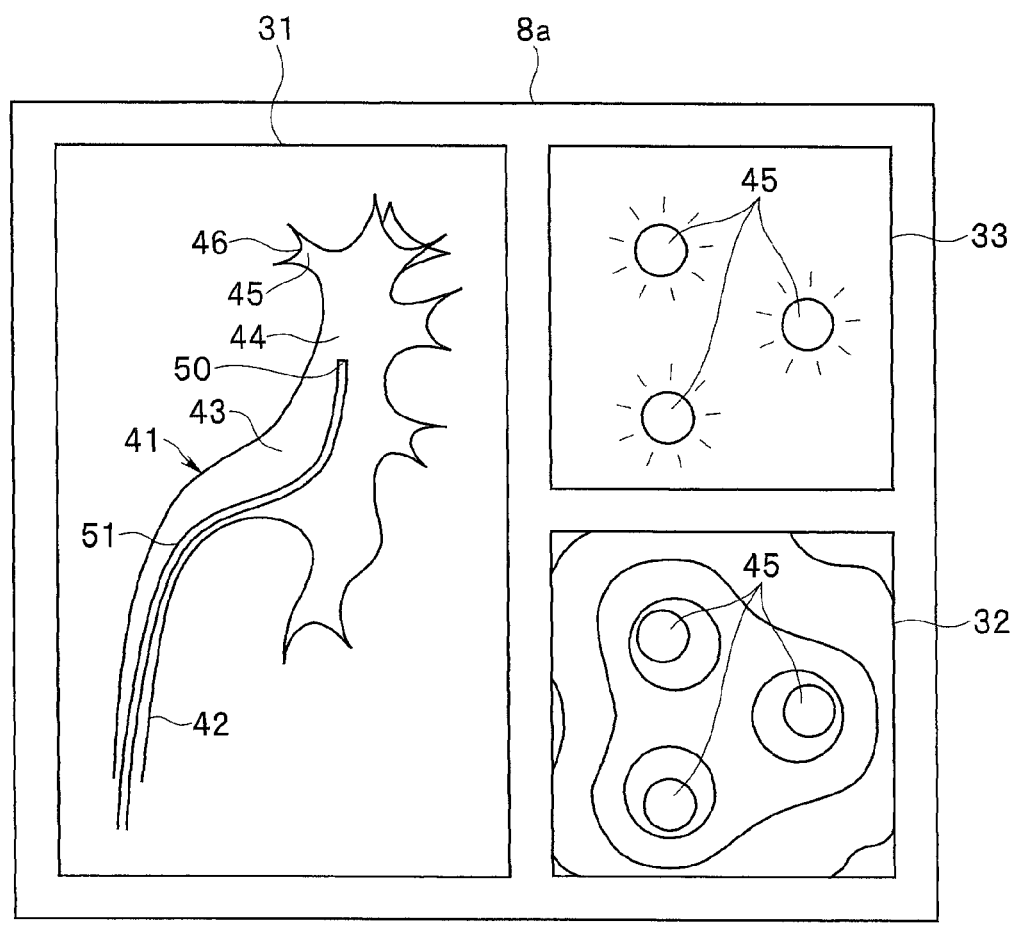
FIG. 4 is a diagram showing a display example of a display screen of a display apparatus in the first embodiment.

Next, FIG. 3 is a flowchart showing operation of the endoscope system 1, and FIG. 4 is a diagram showing a display example of a display screen 8a of the display apparatus 8.

Note that an image displayed on the display screen 8a in FIG. 4 is final two-dimensional image data after being processed by the image processing apparatus 7. Hereinafter, reference numerals of the two-dimensional image data shown in FIG. 4 will be appropriately used to make description.

As shown in FIG. 4, for example, a bird's-eye image 31, a virtual endoscopic image 32 and an endoscopic image 33 are displayed on the display screen 8a of the display apparatus 8. Here, the bird's-eye image 31 is a two-dimensional image of a three-dimensionally observed luminal organ at time of commanding a bird's eye view of the luminal organ constructed as three-dimensional image data. Further, the virtual endoscopic image 32 is a two-dimensional image at time of observing the luminal organ constructed as the three-dimensional image data from a visual point of the objective optical system. The endoscopic image 33 is a picked-up image picked up by the image pickup system 10. Note that the display example shown in FIG. 4 is a mere example, and display of other information, omission of display of some pieces of information and the like may be performed.

On the bird's-eye image 31 shown in FIG. 4, the ureter 42, pelvis of kidney 43, major calyx 44, minor calyxes 45 and renal papillae 46 of the luminal organ 41 are displayed, and, moreover, an insertion portion image 51 showing a current insertion form of the insertion portion 11 as navigation is displayed. A distal end of the insertion portion image 51 is a current objective optical system position 50. In the example shown in the bird's-eye image 31 of FIG. 4, the current objective optical system position 50 is in the major calyx 44.

In the endoscopic image 33 shown in FIG. 4, openings of the plurality of minor calyxes 45 observed from the major calyx 44 are displayed since the objective optical system of the insertion portion 11 is present in the major calyx 44.

Further, in the virtual endoscopic image 32, the openings of the plurality of minor calyxes 45 which should be observed from the current objective optical system position 50 are displayed.

Next, description will be made on a case of using the endoscope system 1 at time of checking whether or not stone fragments remain after a kidney stone is crushed and broken into small parts as an example. In such a check, it is necessary to check everywhere in the lumen of the kidney in order to prevent stone fragments from being overlooked.

At this time, a surgeon performs insertion to a target minor calyx 45 using navigation similar to conventional navigation first. Then, the surgeon performs a check of looking around everywhere in the target minor calyx 45 with the endoscope. In such a check, by the surgeon operating the angle-of-view display button 12b of the operation portion 12 at a desired timing, angle-of-view display is performed.

Further, if judging that observation all inside the one minor calyx 45 has been performed after observing the minor calyx 45 referring to the angle-of-view display, the surgeon moves to a next minor calyx 45 and performs observation using navigation similar to conventional navigation again. If the angle-of-view display is unnecessary at the time of moving between the minor calyxes 45, the surgeon can also operate the angle-of-view display button 12b to turn off the angle-of-view display.

Next, details of the operation of the endoscope system 1 will be described with reference to FIG. 3.

When a process shown in FIG. 3 is started, the luminal organ extracting portion 22 reads out the pieces of preoperative multi-slice image data 16a to 16n to construct three-dimensional image information and, moreover, extracts predetermined luminal organ image information present in the constructed three-dimensional image information as described above (step S1).

On the other hand, the positioning portion 26 acquires position information (position and direction data) about the objective optical system from the position detection apparatus 5 (step S2).

Then, the positioning portion 26 performs positioning between actual space coordinates shown by the acquired position information and three-dimensional image coordinates in which three-dimensional image information is constructed (step S3).

Further, the angle-of-view display information generating portion 27 acquires endoscope specifications data from the CCU 3 and generates angle-of-view display information which includes boundary lines showing an angle-of-view range, based on angle-of-view information included in the endoscope specifications data (step S4).

After that, the image processing portion 23 judges whether or not the angle-of-view display button 12b has been operated to input angle-of-view display instruction data from the CCU 3 (step S5).

Here, if it is judged that the angle-of-view display instruction data has been inputted, the overlapped image creating portion 28 creates an overlapped image obtained by overlapping the insertion portion image 51 and the angle-of-view display information generated by the angle-of-view display information generating portion 27 on a three-dimensional image of a luminal organ extracted by the luminal organ extracting portion 22, based on the position information positioned by the positioning portion 26 (step S6).

On the other hand, if it is judged that the angle-of-view display instruction data has not been inputted, the overlapped image creating portion 28 creates an overlapped image obtained by overlapping the insertion portion image 51 on the three-dimensional image of the luminal organ extracted by the luminal organ extracting portion 22, based on the position information positioned by the positioning portion 26 (step S7).

The image processing portion 23 creates the bird's-eye image 31 from the created overlapped image to configure image data for display together with the virtual endoscopic image 32 and the endoscopic image 33, and outputs the image data to the display apparatus 8. Thereby, an image which includes the bird's-eye image 31, as an overlapped image is displayed on the display apparatus 8 (step S8).

After that, it is judged whether or not to finish this process (step S9). If it is judged that this process is not to be finished, the flow returns to step S2, and a process as described above is repeatedly performed. If it is judged that this process is to be finished, this process is ended.

Figure 5:
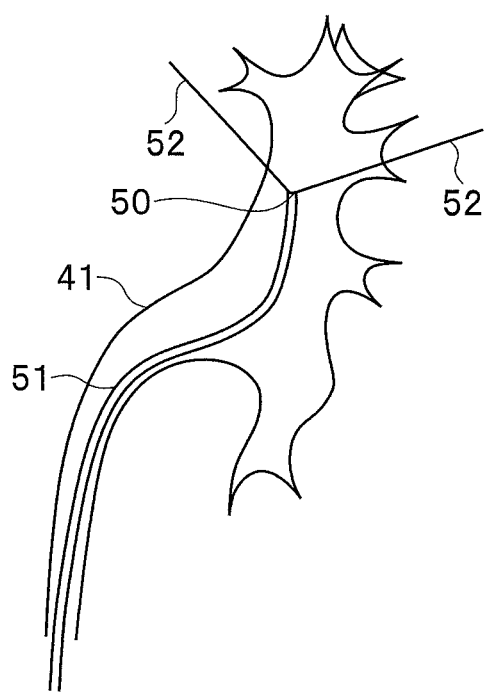
FIG. 5 is a diagram showing an example of a bird's-eye image on which angle-of-view display information is overlapped in the first embodiment.

FIG. 5 is a diagram showing an example of the bird's-eye image 31 on which angle-of-view display information 52 is overlapped.

The angle-of-view display information 52 generated as boundary lines forming a fan shape with an angle showing an angle-of-view range, with the objective optical system position 50 at the distal end of the insertion portion image 51 of the bird's-eye image 31 as a starting point is displayed in a state that the boundary lines extending, gradually being away from each other with a direction corresponding to the optical axis direction of the objective optical system as a center between them.

When the angle-of-view display information 52 displayed as described above is used together with the endoscopic image 33 and the virtual endoscopic image 32, it is possible to discriminate between openings of observed minor calyxes 45 and openings of unobserved minor calyxes 45. That is, if four openings of minor calyxes 45 are present in the bird's-eye image 31 shown in FIG. 5 even though the number of the openings of the minor calyxes 45 displayed in the endoscopic image 33 and the virtual endoscopic image 32 is three in the example shown in FIG. 4, it is judged that an opening of one minor calyx 45 is not observed.

Though the judgment may be performed by the surgeon comparing the bird's-eye image 31 as shown in FIG. 5 and the endoscopic image 33 or the virtual endoscopic image 32, it is also possible to perform a judgment process by the image processing portion 23 and perform display or the like of a judgment result as one of pieces of navigation information.

Figure 6:
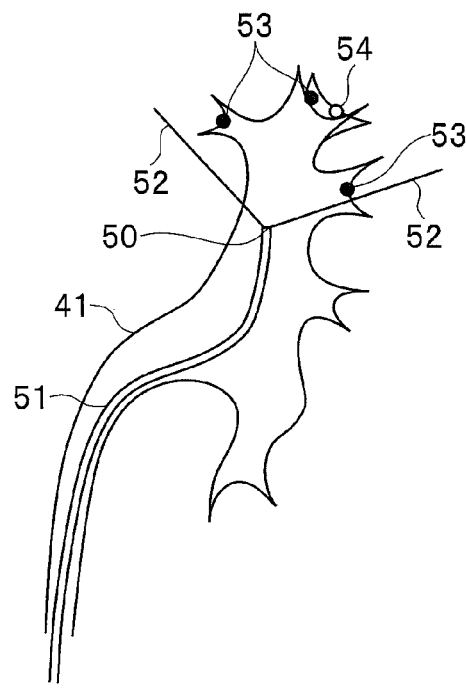
FIG. 6 is a diagram showing an example of giving the bird's-eye image observability/unobservability marks together with the angle-of-view display information in the first embodiment.

FIG. 6 is a diagram showing an example of giving the bird's-eye image 31 observability/unobservability marks together with the angle-of-view display information 52.

That is, as shown in FIG. 6, for example, observability marks 53 and unobservability marks 54 may be displayed at openings of minor calyxes 45 present within a range shown by the angle-of-view display information 52 about the luminal organ 41 in the bird's-eye image 31. However, the display shown in FIG. 6 is an example, and other display aspects may be adopted. Navigation may be performed by voice or in other methods together with display or instead of display.

Figure 7:
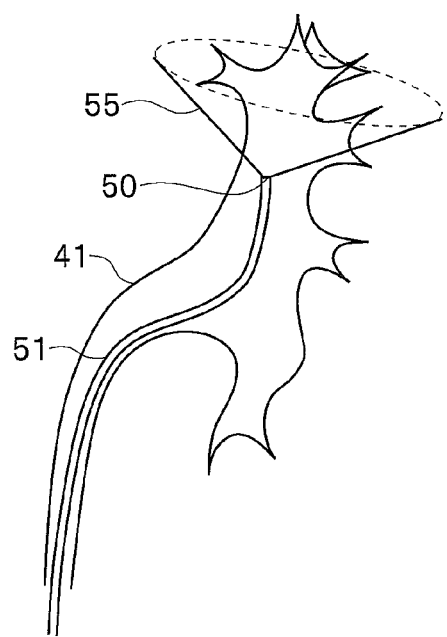
FIG. 7 is a diagram showing another example of the bird's-eye image on which the angle-of-view display information is overlapped in the first embodiment.

Further, FIG. 7 is a diagram showing another example of the bird's-eye image 31 on which the angle-of-view display information 52 is overlapped.

Though the angle-of-view display information 52 shown in FIG. 5 is only the boundary lines forming a fan shape, angle-of-view display information 55 is shown as cone-shaped display information in the example shown in FIG. 7 because an actual observation range is a solid angle range. However, as described above, the angle-of-view display information 55 may be, for example, quadrangular-pyramid-shaped display information in consideration of the shape of the image pickup surface of the image pickup device.

Figure 8:
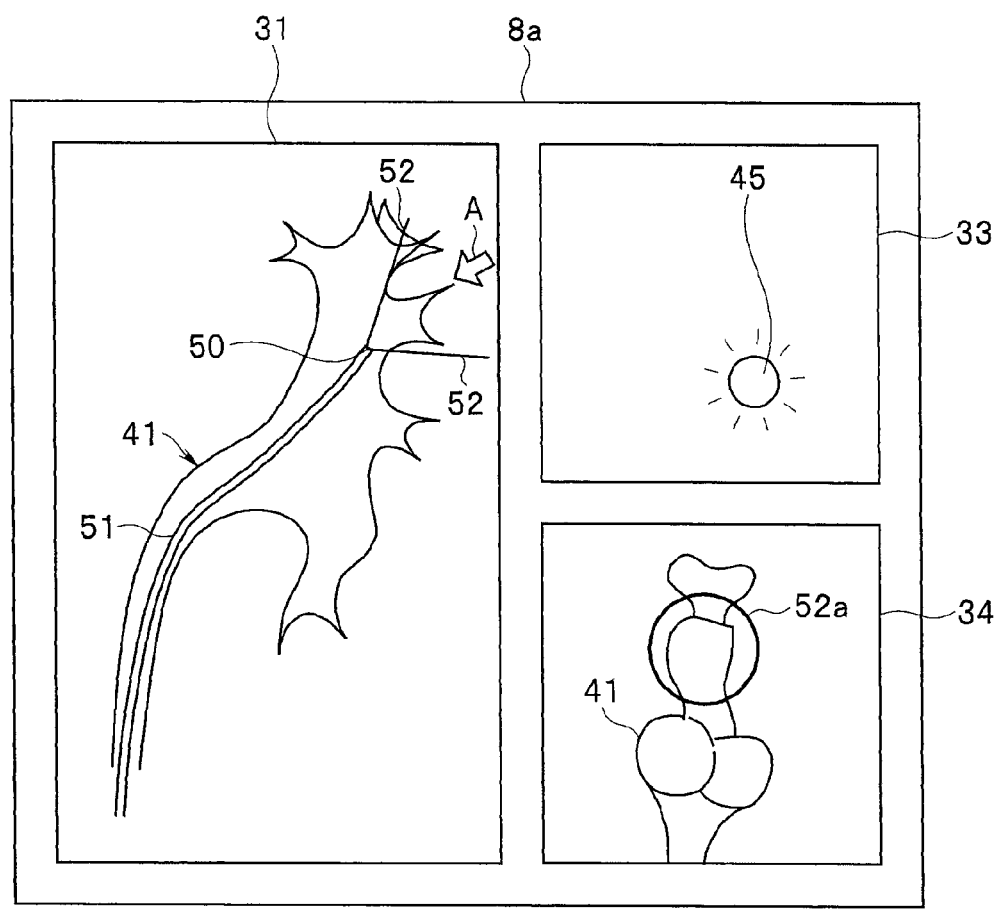
FIG. 8 is a diagram showing an example of displaying the angle-of-view display information on a plurality of bird's-eye images seen from a plurality of different directions in the first embodiment.

Next, FIG. 8 is a diagram showing an example of displaying angle-of-view display information on a plurality of bird's-eye images 31, 34 seen from a plurality of different directions.

The image processing portion 23 is configured to be capable of creating a plurality of two-dimensional overlapped images seen from a plurality of different directions.

In this case, the endoscopic image 33, the bird's-eye image 31, and a second bird's-eye image 34 seen from an angle different from an angle for the bird's-eye image 31 are displayed on the display screen 8a of the display apparatus 8. Note that, though the second bird's-eye image 34 is displayed instead of the virtual endoscopic image 32 in the example shown in FIG. 8, the second bird's-eye image 34 may be displayed in addition to the bird's-eye image 31, the virtual endoscopic image 32 and the endoscopic image 33.

Here, the second bird's-eye image 34 is an image at time of commanding a bird's eye view from a direction of an arrow A in FIG. 8, and the image is generated by the image processing portion 23 rotating the luminal organ constructed as three-dimensional image information in the three-dimensional coordinates.

Then, the angle-of-view display information 52 configured with boundary lines with a predetermined length forming a fan shape is displayed in the bird's-eye image 31 similarly to FIG. 5, and angle-of-view display information 52a showing an angle-of-view range in a shape at time of distal ends of the boundary lines being seen from the direction of the arrow A, for example, in a circular shape is displayed in the second bird's-eye image 34. Note that the angle-of-view display information 52a may be, for example, in a quadrangle shape in consideration of the shape of the image pickup surface of the image pickup device, similarly as described above.

Thus, it becomes possible to three-dimensionally grasp an observation range by displaying the pieces of angle-of-view display information 52, 52a in the plurality of bird's-eye images 31, 34 seen from a plurality of different directions.

Figure 9:
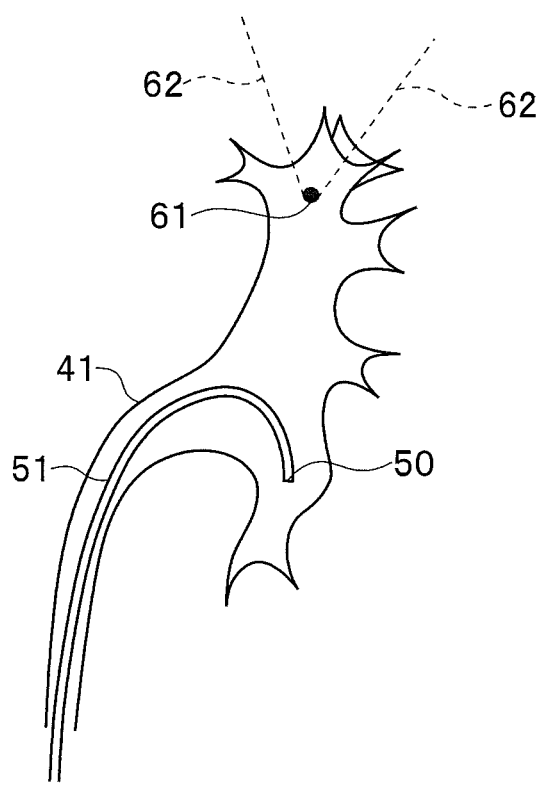
FIG. 9 is a diagram showing an example of the angle-of-view display information displayed when a freeze angle-of-view display button is operated in the first embodiment.

Next, FIG. 9 is a diagram showing an example of the angle-of-view display information displayed when the freeze angle-of-view display button 12c is operated.

As described above, when the angle-of-view display button 12b is operated, the angle-of-view display information is displayed in real time with the current objective optical system position 50 as a starting point.

In comparison, when the freeze angle-of-view display button 12c, which is the acquisition instruction portion, is operated, angle-of-view display information at a time point of the freeze angle-of-view display button 12c being operated continues to be displayed while the freeze angle-of-view display instruction is effective.

That is, when freeze angle-of-view display instruction data is inputted to the image processing portion 23, the image reading-out portion 29 reads out a two-dimensional overlapped image, or position information and angle-of-view information, at a time point of starting to input the acquisition instruction from the second storage portion 24. Therefore, the freeze angle-of-view display button 12c is the acquisition instruction portion configured so that an acquisition instruction for acquiring information from the second storage portion 24 is inputted.

Here, if the read-out data is the position information and the angle-of-view information, the image processing apparatus 7 reads out the pieces of preoperative multi-slice image data 16a to 16n from the server 6, positions the position information and angle-of-view information read out from the second storage portion 24 by the positioning portion 26, and, after that, creates a two-dimensional overlapped image at the time point of starting to input the acquisition instruction.

The image reading-out portion 29 is adapted to continue to output the two-dimensional overlapped image at the time point of starting to input the acquisition instruction, which has been read out or created based on read-out information, to the display apparatus 8 for display while the acquisition instruction is effective.

Thereby, as shown in FIG. 9, even if the objective optical system position 50 changes after the freeze angle-of-view display button 12c is operated, angle-of-view display information 62 continues to be freeze-displayed with an objective optical system position 61 at a time point of the freeze angle-of-view display button 12c being operated as a starting point.

The freeze display is eliminated from the screen at a time point when, after that, the freeze angle-of-view display button 12c is operated to cancel the freeze angle-of-view display instruction.

Figure 10:
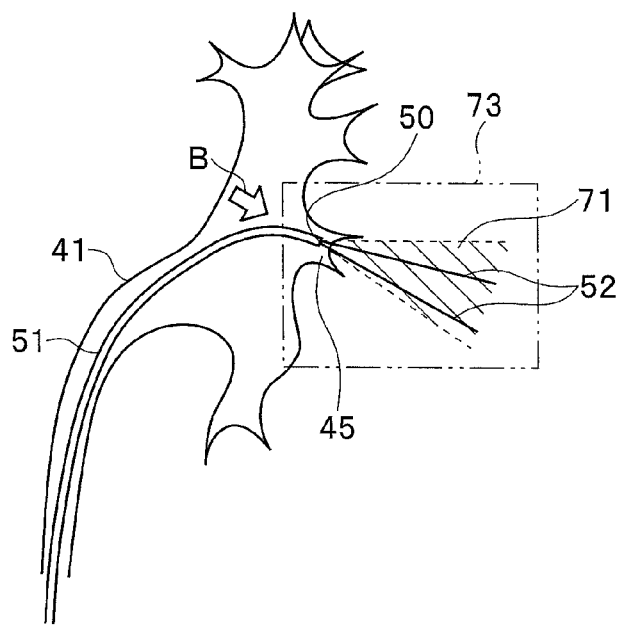
FIG. 10 is a diagram showing an example of the angle-of-view display information displayed on the bird's-eye image when an accumulated angle-of-view display button is operated in the first embodiment.
Figure 11:
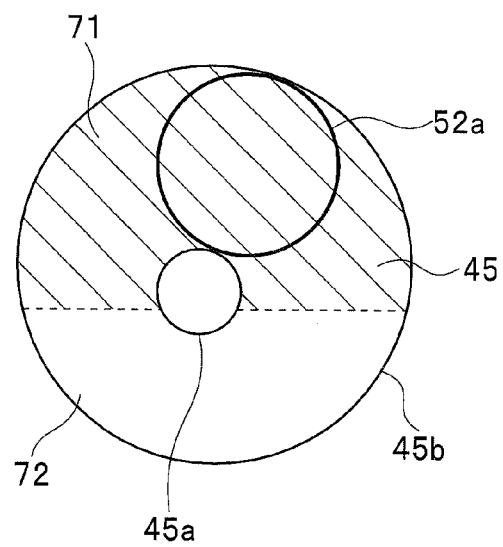
FIG. 11 is a diagram showing an example of the angle-of-view display information displayed on a bird's-eye image seen from a different direction when the accumulated angle-of-view display button is operated in the first embodiment.

Next, FIG. 10 is a diagram showing an example of the angle-of-view display information displayed on the bird's-eye image when the accumulated angles-of-view display button 12d is operated, and FIG. 11 is a diagram showing an example of the angle-of-view display information displayed on a bird's-eye image seen from a different direction when the accumulated angles-of-view display button 12d is operated. Here, FIG. 11 is an image seen from a direction of an arrow B in FIG. 10.

When the accumulated angle-of-view display button 12d, which is the accumulated display instruction portion, is operated to input an accumulated angle-of-view display instruction, past pieces of angle-of-view display information are displayed, being accumulated.

First, the second storage portion 24 has stored at least one of two-dimensional overlapped images, and pieces of position information and angle-of-view information at a plurality of past time points. Note that, since it is possible to reset the accumulated angle-of-view display, two-dimensional overlapped images acquired at time points before the reset operation and position information and angle-of-view information acquired at time points before the reset operation may be eliminated when a reset operation is performed.

Then, if an accumulated angle-of-view display instruction is inputted, the image processing portion 23 reads out at least one of accumulated two-dimensional overlapped image obtained by accumulatively overlapping two-dimensional overlapped images at a plurality of past time points, and the position information and angle-of-view information at a plurality of past time points, from the second storage portion 24.

Here, if what is read out from the second storage portion 24 is the position information and angle-of-view information at the plurality of past time points, the image processing apparatus 7 reads out the pieces of preoperative multi-slice image data 16a to 16n from the server 6, positions the position information and angle-of-view information at the plurality of past time points which have been read out from the second storage portion 24 by the positioning portion 26 and, after that, creates two-dimensional overlapped images at the plurality of past time points.

After that, the image processing portion 23 accumulatively overlaps the two-dimensional overlapped images at the plurality of past time points read out from the second storage portion 24 or created based on the position information and angle-of-view information read out from the second storage portion 24 to create an accumulated two-dimensional overlapped image in which past angles-of-view are displayed being accumulated.

In this way, the accumulated two-dimensional overlapped image, for example, as shown in FIG. 10 or 11 is displayed on the display apparatus 8.

First, FIGS. 10 and 11 show a state at time of observing, from an opening 45a of a minor calyx 45, an inside of the minor calyx 45. In this example, the inside 45b of the minor calyx 45 is wider than the opening 45a.

Accumulated angle-of-view display information 71 shown by hatching shows an observed angle-of-view range in the inside 45b of the minor calyx 45.

Further, the pieces of angle-of-view display information 52, 52a show a range of the inside 45b of the minor calyx 45 observed from the current objective optical system position 50.

On the other hand, an area 72 shows an unobserved area in the minor calyx 45.

Note that it is recommended to, in a case of attempting to observe everywhere in such a particular small area (here, the minor calyx 45), enlarge and display an area which includes the particular small area, that is, an enlargement target area 73 as shown by a two-dot chain line in FIG. 10. For example, automatically enlarging and displaying the enlargement target area 73, and the like may be performed while the accumulated angle-of-view display button 12d has been operated and an accumulated angle-of-view display instruction is effective.

According to the first embodiment, since an overlapped image obtained by overlapping angle-of-view display information at a position positioned by the positioning portion 26 in a luminal organ image is created, it becomes possible to understandably present an observation range in a luminal organ.

Further, since the second storage portion 24 configured to store at least one of a two-dimensional overlapped image, and position information and angle-of-view information is provided, it becomes possible to confirm an observation range at a certain time point at a later time point. Especially, in the case of storing position information and angle-of-view information, it becomes possible to reduce storage capacity in comparison with the case of storing a two-dimensional overlapped image.

Moreover, since the storage of at least one of a two-dimensional overlapped image, and position information and angle-of-view information by the second storage portion 24 is performed in association with a picked-up image picked up by the image pickup system 10, it becomes possible to, when a picked-up image is picked up as a record photograph to be put on a patient's chart or the like, easily grasp an image pickup range of the record photograph by referring to an associated two-dimensional overlapped image or a two-dimensional overlapped image created from associated position information and angle-of-view information.

At this time, if the storage of at least one of a two-dimensional overlapped image, and position information and angle-of-view information associated with a picked-up image, by the second storage portion 24 is performed when an image pickup instruction is inputted from the image pickup instruction portion (that is, if a timing of the image pickup instruction being inputted from the release button 12a, which is the image pickup instruction portion, is included in a timing of performing the associated storage), it becomes possible to certainly grasp an image pickup range at a time point of the picked-up image being acquired.

Further, since the image reading-out portion 29 is adapted to continue to output a two-dimensional overlapped image at a time point of starting to input an acquisition instruction which is read out from the second storage portion 24 in response to the acquisition instruction or a two-dimensional overlapped image created based on position information and angle-of-view information at the time point of starting to input the acquisition instruction which is read out from the second storage portion 24 in response to the acquisition instruction while the acquisition instruction is effective, it becomes possible to continuously see an observation range at a time point of a freeze angle-of-view display instruction being given, during a period during while freeze display is effective. Thereby, even if the current objective optical system position 50 changes, for example, minutely, it is possible to stably see an observation range at the time point of the freeze angle-of-view display instruction.

Additionally, in a case where the image processing portion 23 creates an overlapped image in response to position information being acquired by the position detection apparatus 5, it becomes possible to display angle-of-view display information in real time. Further, it also becomes possible to accumulate overlapped images for performing accumulated angle-of-view display in advance.

Since the image processing portion 23 is adapted to generate an overlapped image when turning on overlapped image generation is selected by the angle-of-view display button 12b and not to generate an overlapped image when turning off overlapped image generation is selected, an overlapped image is generated only when real time display is required, and it becomes possible to reduce a processing load when real time display is not required.

If the display apparatus 8 is adapted to display an overlapped image while overlapped image generation is turned on by a selection instruction, it becomes possible to observe angle-of-view display information displayed in real time. Further, even in a case of a surgeon who does not want angle-of-view display information to be continuously displayed being overlapped, it becomes possible to desirably switch on/off of display of the angle-of-view display information by selecting on/off of overlapped image generation.

Further, in the case of creating and displaying a plurality of two-dimensional overlapped images seen from a plurality of different directions as shown in FIG. 8, it becomes possible to three-dimensionally grasp an observation range.

Moreover, since the angle-of-view display information is adapted to include boundary lines showing an angle-of-view range, which extend with a position of the objective optical system shown by position information as a starting point, it becomes possible to easily grasp a range observed from the position of the objective optical system.

Since the image processing portion 23 is adapted to create an accumulated two-dimensional overlapped image obtained by accumulatively overlapping two-dimensional overlapped images at a plurality of past time points when an accumulated angle-of-view display instruction is inputted, it becomes possible to easily confirm areas observed in the past and unobserved areas.

Second Embodiment

Figure 12:
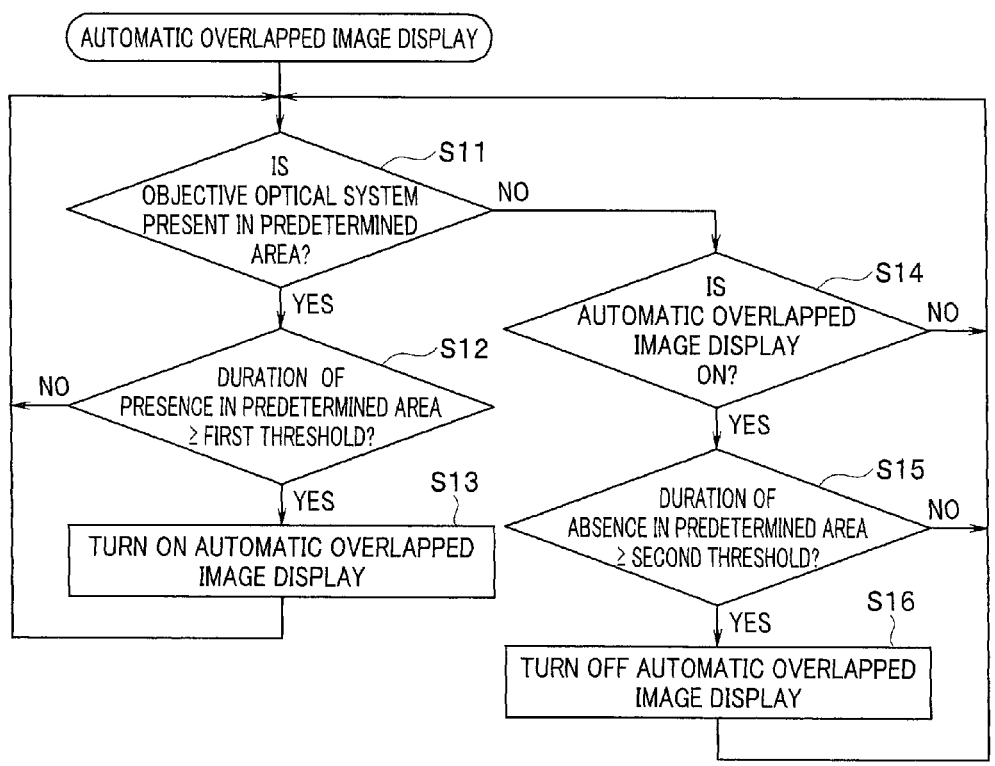
FIG. 12 is a flowchart showing an automatic overlapped image display process in an endoscope system of a second embodiment of the present invention.

FIG. 12 shows a second embodiment of the present invention and is a flowchart showing an automatic overlapped image display process in the endoscope system 1. In the second embodiment, portions similar to those in the first embodiment described above are given same reference numerals, and description of the portions is appropriately omitted. Description will be made mainly only on different points.

Though display of an overlapped image, that is, display of angle-of-view display information is performed in response to a button operation from a surgeon in the first embodiment described above, the present invention is such that the display is performed by an automatic process.

That is, when the process shown in FIG. 12 is started, it is judged whether or not the objective optical system is present in a predetermined area, for example, in a minor calyx 45 (step S11).

Here, if it is judged that the objective optical system is present in the predetermined area, it is judged whether or not a duration while the objective optical system is present in the predetermined area is equal to or above a first threshold (step S12).

Here, if it is judged that the duration is equal to or above the first threshold, automatic overlapped image display is turned on (step S13), and then the flow returns to the judgment of step S11. If it is judged that the duration is below the first threshold, the flow returns to the judgment of step S11 without performing the process of step S13. Here, when the automatic overlapped image display is turned on at step S13, such a process of creating and displaying an overlapped image in real time as described in the first embodiment described above is performed.

Further, if it is judged at step S11 that the objective optical system is absent in the predetermined area, it is judged whether or not the automatic overlapped image display is currently turned on (step S14).

Here, if it is judged that the automatic overlapped image display is turned on, it is judged whether or not a duration while the objective optical system is absent in the predetermined area is equal to or above a second threshold (step S15).

Here, if it is judged that the duration is equal to or above the second threshold, the automatic overlapped image display is turned off (step S16), and then the flow returns to the process of step S11. If it is judged at step S14 that the automatic overlapped image display is off, and if it is judged at step S15 that the duration is below the second threshold, the flow returns directly to the process of step S11.

According to the second embodiment as described above, effects almost similar to effects of the first embodiment described above are provided. Further, since an overlapped image is automatically created when a duration while the objective optical system is present in a predetermined area is equal to or above the first threshold, it becomes possible to, at the time of observing a particular area such as the minor calyx 45, grasp an observed range without trouble of performing a manual operation being required.

Moreover, since an overlapped image continues to be automatically created while the duration while the objective optical system is absent in the predetermined area is below the second threshold, it is possible to prevent on/off of display of angle-of-view display information from being unstably switched in vicinity of an entrance of a particular area such as the minor calyx 45 and perform observation seeing a stable display screen.

Since overlapped image display is turned off if the duration while the objective optical system is absent in the predetermined area is equal to or above the second threshold, it becomes possible to perform movement of an insertion position and the like while seeing a screen on which angle-of-view display information is not displayed, without the trouble of performing a manual operation being required.

Note that, though description has been made above mainly on an endoscope system, an endoscope system operation method for operating the endoscope system in such a manner as described above, a program for causing a computer to execute the operation method, a non-temporary computer-readable recording medium in which the program is recorded, and the like are also conceivable.

Further, the present invention is not limited to the embodiments described above as they are, and components can be modified and embodied at an implementation stage within a range not departing from the spirit of the present invention. Further, various aspects of the invention can be formed by appropriate combinations of the plurality of components disclosed in the above embodiments. For example, some components may be deleted from all the components shown in the embodiments. Moreover, components between the different embodiments may be appropriately combined. Thus, various modifications and applications are, of course, possible within the range not departing from the spirit of the invention.

What is claimed is:

1. An endoscope system comprising:
   an endoscope having an insertion portion to be inserted into a subject;
   an objective optical system provided in the insertion portion and configured to form an optical image of an inside of the subject; and
   one or more processors comprising hardware, wherein the one or more processors are configured to:
      acquire position information about the objective optical system;
      position the position information about the objective optical system relative to three-dimensional image information related to the subject;
      generate angle-of-view display information showing angle-of-view information about a picked-up image picked up by an image pickup system including the objective optical system; and
      automatically create an overlapped image obtained by overlapping the angle-of-view display information at a position on the three-dimensional image information corresponding to the position information about the objective optical system, if a duration while the objective optical system is judged to be present in a predetermined area is equal to or above a first threshold based on the position information, after the duration until a duration while the objective optical system is judged to be absent in the predetermined area is equal to or above a second threshold.

2. The endoscope system according to claim 1,
   wherein the one or more processors are configured to:
      output an accumulated angle-of-view display instruction signal for accumulating and displaying past angle-of-view display information; and
      when the accumulated angle-of-view display signal is inputted, create an accumulated overlapped image obtained by accumulatively overlapping overlapped images obtained by overlapping the angle-of-view display information at a plurality of past time points on the three-dimensional image information.

3. The endoscope system according to claim 1,
   wherein the one or more processors are configured to:
      create a two-dimensional overlapped image from the overlapped image; and control a storage to store at least one of the two-dimensional overlapped image, and the position information and the angle-of-view information.

4. The endoscope system according to claim 3, wherein the one or more processors are configured to control the storage to store at least one of the two-dimensional overlapped image, and the position information and the angle-of-view information in association with the picked-up image.

5. The endoscope system according to claim 1, wherein the one or more processors are configured to create the overlapped image in response to the position information being acquired by the one or more processors.

6. The endoscope system according to claim 1, wherein the one or more processors are configured to:
receive a selection instruction for selecting on/off of overlapped image generation; and
generate the overlapped image when the overlapped image generation is turned on by the selection instruction and does not generate the overlapped image when the overlapped image generation is turned off by the selection instruction.

7. The endoscope system according to claim 6, wherein the one or more processors are configured to:
control a display to display the overlapped image while the overlapped image generation is turned on by the selection instruction.

8. The endoscope system according to claim 1, wherein the angle-of-view display information includes boundary lines showing an angle-of-view range, the boundary lines extending with a position of the objective optical system shown by the position information as a starting point.

9. The endoscope system according to claim 1, wherein the one or more processors are configured to create a plurality of two-dimensional overlapped images seen from a plurality of different directions, from the overlapped image.

* * * * *